United States Patent [19]

McDonald

[11] Patent Number: 4,601,037
[45] Date of Patent: Jul. 15, 1986

[54] PULSED LASER SYSTEM

[75] Inventor: John J. McDonald, San Marino, Calif.

[73] Assignee: Britt Corporation, Los Angeles, Calif.

[21] Appl. No.: 620,345

[22] Filed: Jun. 13, 1984

[51] Int. Cl.[4] .............................................. H01S 3/10
[52] U.S. Cl. ...................................... 372/25; 372/38; 372/30
[58] Field of Search ................... 372/25, 26, 29, 8, 30, 372/32, 38, 69

[56] References Cited

U.S. PATENT DOCUMENTS

| | | |
|---|---|---|
| 3,481,340 | 6/1965 | McKnight et al. . |
| 3,727,061 | 4/1973 | Dworkin ................. 372/8 |
| 3,747,019 | 7/1973 | Koechner et al. ..... 372/30 |
| 3,928,815 | 12/1975 | Hellwarth . |
| 3,971,382 | 7/1976 | Krasnov . |
| 4,009,385 | 2/1977 | Sell ........................ 372/29 |
| 4,053,845 | 10/1977 | Gould . |
| 4,161,436 | 7/1979 | Gould . |
| 4,243,951 | 1/1981 | Wolkstein et al. ..... 372/26 |
| 4,359,773 | 11/1982 | Swartz et al. .......... 372/29 |
| 4,409,979 | 10/1983 | Roussel et al. . |
| 4,412,331 | 10/1983 | Chapman ............... 372/29 |

Primary Examiner—Léon Scott, Jr.
Attorney, Agent, or Firm—Lawrence S. Levinson; Robert E. Lee, Jr.

[57] ABSTRACT

A pulsed laser system capable of operating in a plurality of modes for delivering a burst of laser pulses to a target wherein the pulse width of the laser pulses are automatically controlled in response to the mode selected. A special calibration procedure allows the system to determine the pulse width and pulse repetition rate when the laser is producing a predetermined power output level as measured by a power meter at the target site. Using calibrated pulse width and pulse repetition rate, the pulse width and pulse repetition rate of the laser pulses to be delivered to the target for any particular treatment burst can be determined. Means are provided for determining the energy delivered to the target for any particular treatment burst. A potentiometer coupled to a laser spot size control lense assembly provides a signal proportional to the spot size. From this signal and the energy delivered, the energy density can be calculated. A special REPEAT mode allows the operator to repeat automatically at preselected intervals the firing of bursts of laser pulses characterized by repetition rate, pulse width and exposure time. The bursts will be repeated for as long as the foot pedal is depressed.

3 Claims, 10 Drawing Figures

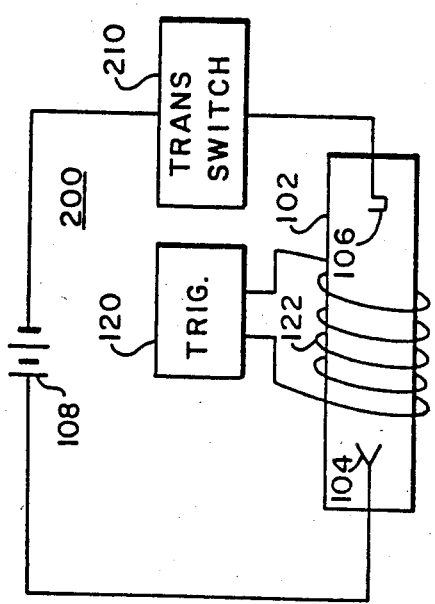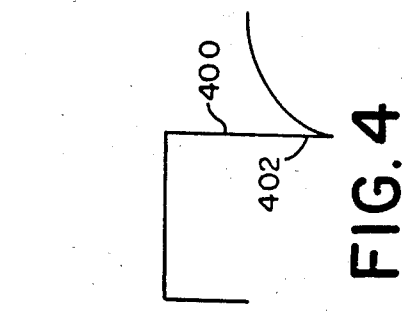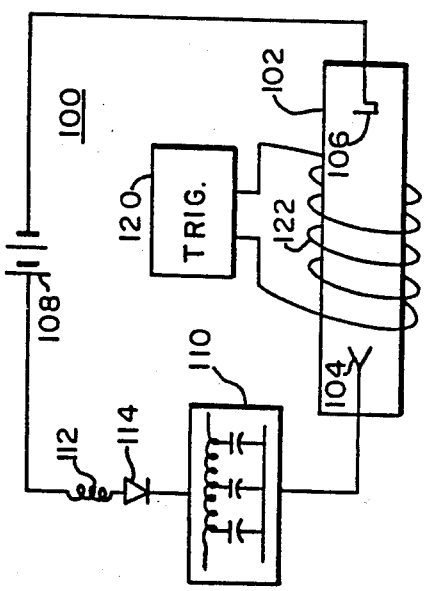

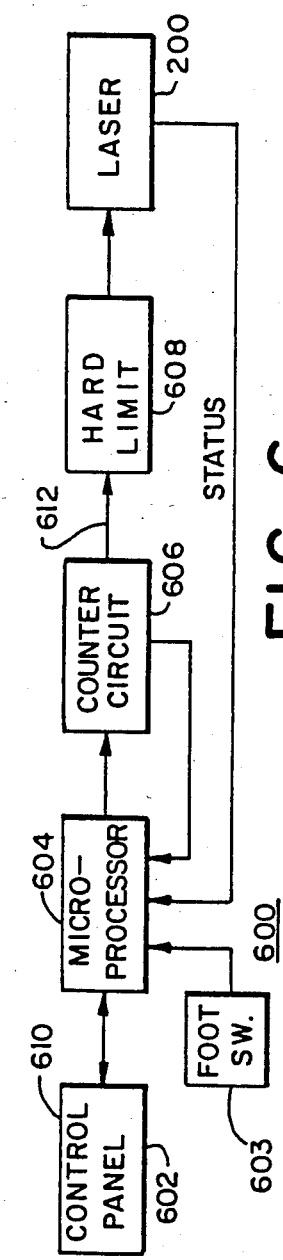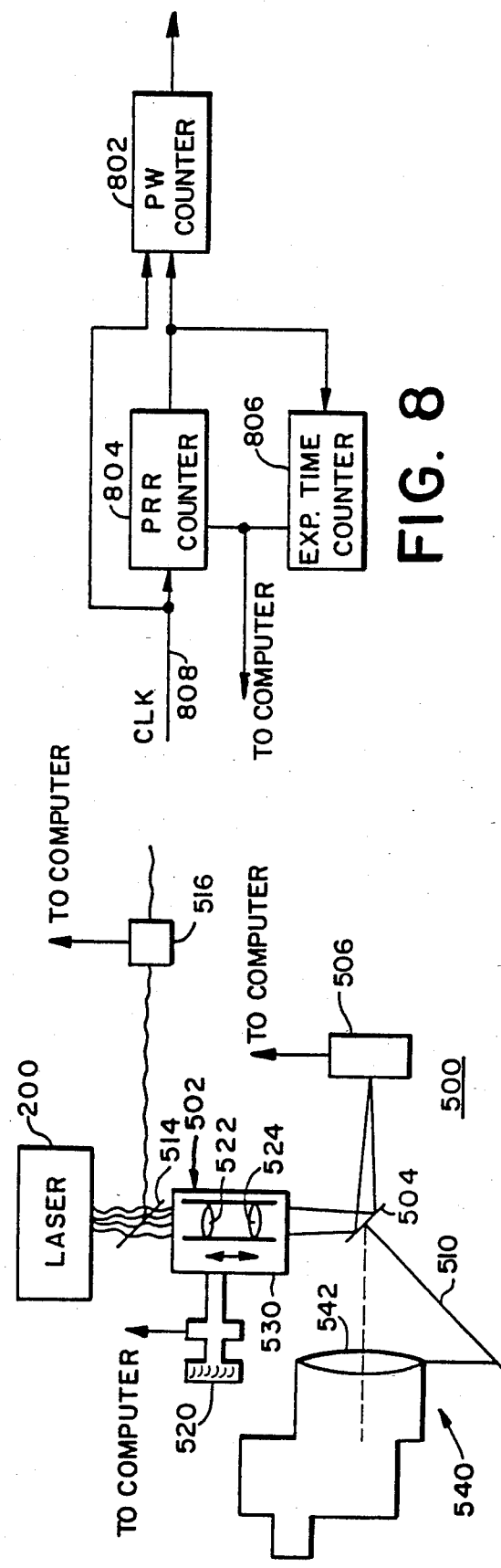

PULSED LASER SYSTEM

BACKGROUND OF THE INVENTION

The present invention relates to a pulsed laser system, more particulary, to a control circuit for providing variable pulse width control signals to the laser to control its output.

Prior art pulsed lasers use an LC pulse forming network connected to the anode of the tube to store the energy for the laser pulse. A trigger circuit applies a triggering pulse to a coil wrapped around the laser tube which ionizes the argon gas within the tube. This provides a discharge path for the energy stored in the pulse forming network through the laser tube to the cathode causing the tube to lase. However, the laser pulse width is fixed by the LC constant of the PFN. The pulse repetition rate is controlled by the triggering pulses, but the pulse width remains fixed.

When performing perforation procedures such as iridotomies, it is desirable to provide a finite number of high power pulses with predetermined pulse widths. When performing thermal procedures such as coagulation, it is desirable to provide near CW tube operation at relatively low power levels which requires a combination of pulse width and repetition rate to control the energy being delivered. A pulse width which is fixed and optimized for perforation procedures will not in general be optimzed for coagulation procedures.

It is desirable, therefore, to provide a pulsed laser which provides laser pulses with pulse width and repetition rate which vary over a relatively wide range.

When using pulsed lasers in a therapeutic laser system such as in the treatment of the eye, it is also desireable to determine the energy and energy density delivered to the eye during treatment. Because the power of the laser output is adjusted by varying pulse width and repetition rate it is also highly desireable to simplify the requirements of the operator's inputs when using the variable pulse width pulsed laser by providing automatic determination of optimum pulse width.

Finally, it is highly desireable to reduce operator fatigue encountered in lengthy treatment procedures.

SUMMARY OF THE INVENTION

The present invention is directed to a pulse laser system comprising a power switching circuit for providing drive signals to a pulsed laser to generate a burst of laser pulses suitable for a particular treatment. The burst is generated in response to a series of control signals which in turn are generated by a control circuit which sets the pulse repetition rate, pulse width and exposure time of the control signals.

A treatment switch such as a foot pedal or other suitable means is movable between off and on positions for causing the control signals to be applied to the laser thereby generating the burst of laser pulses. Means are provided for automatically repeating the burst of laser pulses at a predetermined interval which the treatment switch remains in the on position.

BRIEF DESCRIPTION OF THE DRAWINGS

FIG. 1 is a block diagram schematic of a prior art pulsed laser.

FIG. 2 is a block diagram schematic of an improved pulsed laser

FIG. 3 is a more detailed schematic of a switching portion of the improved pulsed laser of FIG. 2.

FIG. 4 is a representation of a switching signal output of a portion of the schematic of FIG. 3.

FIG. 5 is a simplified block diagram of a portion of an ophthalmic laser system.

FIG. 6 is a simplified block diagram of a control circuit portion of an ophthalmic laser system shown coupled to a laser.

FIG. 8 is a more detailed block diagram of the counter circuit portion of the control circuit of FIG. 6.

DETAILED DESCRIPTION OF THE DRAWINGS

Figure 7:
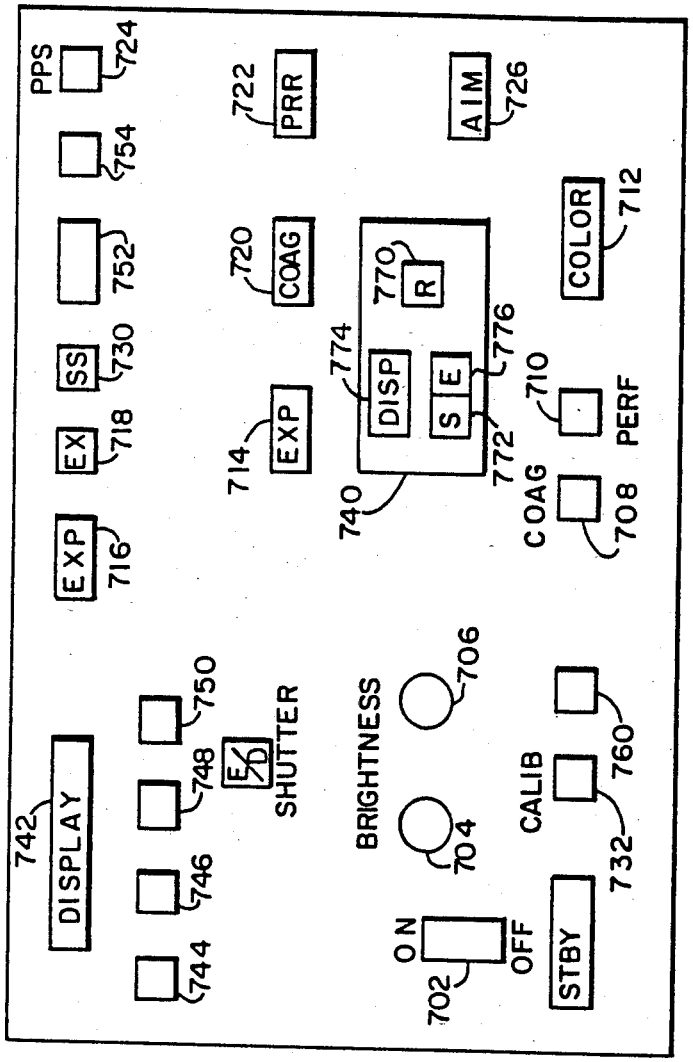
FIG. 7 is a detailed representation of the control panel portion of FIG. 6.

FIG. 1 is a schematic representation of a prior art pulsed laser designated generally 100. It comprises an argon laser tube 102 having a cathode 106 and anode 104. A voltage V from voltage source 108 is applied to the cathode 106 and anode 104 through a pulse forming network (PFN) 110. An inductor 112 and diode 114 are placed in series between the voltage source 108 and one terminal of PFN 110. The laser 100 further comprises a trigger circuit 120 coupled to a wire coil 122 which surrounds tube 102. For an example of a pulsed gas laser with radiation coupling, see U.S. Pat. No. 3,626,325.

The PFN 110 is a conventional LC filter arrangement comprised of inductors and capacitors. By selecting properly the inductance, L, and the capacitance, C, the pulse width of the laser pulse can be defined. However, once the PFN 110 is designed, the pulse width becomes fixed.

The PFN 110 stores a fixed amount of energy from voltage source 108. When the trigger circuit 120 applies a voltage pulse across coil 122, the argon gas within tube 102 is ionized. The ionized gas provides a pathway through which the energy in the PFN 110 can discharge from the cathode 106 to anode 104 causing the laser to lase until the energy in the circuit is depleted. The PFN 110 begins to store energy once again but it will not discharge until the trigger circuit pulses the coil again. The pulse width of the laser output pulse is fixed and determined by the LC constant of the PFN 110 while the triggering circuit 120 determines the pulse repetition rate of the pulses. The pulse repetition rate can be varied by the triggering pulses, there being a limit on the maximum rate determined by the design of the PFN 110.

FIG. 2 is a schematic representation of a pulsed laser designated generally 200 and suitable for use as the laser 200 in FIGS. 5 and 6. It comprises the tube 102 of FIG. 1 with cathode 106, anode 104 and voltage source 108. It further comprises a new power transistor switching circuit 210 and the trigger circuit 120 with coil 122 of FIG. 1. The power switching circuit 210 replaces the PFN 110 and inductor-diode combination 112 and 114 of FIG. 1. With the power switching circuit 210, it is possible to generate variable pulse width laser output pulses. Since the pulse repetition rate is also determined by the switching circuit 210, the trigger circuit 120 is pulsed one time to ionize the gas and thereafter remains on continuously at a lower power level in a glow mode.

There are several critical requirements that the power switching circuit 210 must meet. The first is the ability to provide a variable pulse width laser output. The range of pulse width variation is defined by the intended modes of operation of the laser. For example, it has been found that when using a pulsed laser in a perforation procedure, such as an iridotomy, a series of pulses each with a pulse width of 120 microseconds performs well. When performing a coagulation procedure, a relatively rapid pulse repetition rate with smaller pulse widths, such as 30 microsecond pulse widths, are desirable. The 30 microsecond pulse width is not as likely to cause perforation. Therefore, it is desirable to provide variable pulse widths from at least 30 microseconds to 120 microseconds. Secondly, the power switching circuit 210 must be capable of providing a large current (e.g. 100 amps) to the laser tube 102 during lasing. The current is a function of the impedance of the tube 102 and voltage across the tube, V. Typically, the impedance of the tube is four ohms resistive and the voltage is 500 volts. Finally, it is desirable to use a pulsed transformer to drive the power transistor because a transformer provides a sharp pulse termination with a negative going voltage at the pulse trailing edge.

FIG. 3 is a detailed schematic of the power switching circuit 210 of FIG. 2. The circuit comprises of ferroresonant transformer circuit designated generally 300 comprising a first pair of primary coils 302 and 304 coupled to input terminals 301 and 303 via a switch 306; a second set of primary coils 308 and 310 wound oppositely from the first primary pair and coupled to the input terminals; a pair of secondary coils 312 and 314; and iron cores 316 and 318. The secondary coils 312 and 314 are in series and are coupled to three parallel power transistor output circuits designated generally 322, 324, and 326.

It is the function of the transformer circuit 300 to provide switching signals to the transistor circuits with a variable pulse width in response to pulsed control signals applied to switch 306. To drive the transistor circuits a 6 V 15–20 amp switching signal is required. As mentioned earlier the pulse width must be variable over at least a 30 microsecond to 120 microsecond range.

The maximum pulse width of the output from any transformer is a function of the voltage and time. A transformer that is pulsed will saturate at some fundamental limit of the transformer. For example, a pulse transformer suitable for a pulsed argon laser system will saturate at a 30 microsecond pulse width. To double the pulse width a pair of primary windings 302 and 304 and associated secondary windings 312 and 314, respectively, are used. This halves the voltage across each winding and doubles the overall pulse width to 60 microseconds before saturation occurs. It is possible to double the pulse width again to 120 microseconds by recognizing that the ferroresonant transformer follows a magnetic hysteresis curve. If it is repeatedly pulsed in a unipolar direction only one half the hysteresis curve is being used before the core saturates and hence the pulse width is one half of what is could be if the entire hysteresis curve were utilized. The core saturates in one direction but is never driven into saturation in the reverse direction between pulse intervals because no reverse energy is ever applied to the winding.

In the present invention, a 50 volt potential is constantly applied to the input terminals 301 and 303. While switch 306 is open the 50 volts is applied through 50 ohm resistor 320 to the second pair of primary windings 308 and 310. This biases the cores 316 and 318 into saturation in one direction. Remember the windings 308 and 310 are wound oppositely from the primary windings 302 and 304. When it is desired to apply a pulsed control signal to the transistor switching circuit 210 to pulse the laser, switch 306 is closed for the duration of the desired pulse width and the 50 volts is applied to the windings 302 and 304. Because the cores 316 and 318 were driven into saturation in one direction by windings 308 and 310, when the control pulse is applied to the switch 306 it takes twice as long to drive the cores 316 and 318 into saturation in the direction of the first pair of primary windings 302 and 304. This doubles the pulse width. Hence, a range of pulse widths from less than 30 microseconds duration up to pulse widths of 120 microseconds are possible with the arrangement of FIG. 3.

All of the transistor circuits are identical and only circuit 322 will be described in detail. Circuit 322 comprises a Motorola MJ10016 power transistor 330. The base of the transistor is coupled through a pair of diodes 332 and 334 and a 0.10 ohm resistor 336 to an output terminal 337 of the secondary winding pair 312 and 314. The emitter of the transistor 330 is coupled through a 0.02 ohm resistor 338 to the remaining output terminal 339 of the secondary winding pair. The collector is coupled to the cathode of the laser tube and also through diode 340 to the resistor 336. Finally the base is coupled along an alternate path through diode 342 to the resistor 336.

The collector diode 340 and one of the base diodes of pair 332 and 334 simulate a transistor coupled to transistor 330 to form a Darlington transistor circuit. As is well known in the art, the second transistor (in this case the power transistor 330) is kept from saturating by the action of the first transistor (in this case the diode pair 340 and either 332 or 334). This results in quicker switching action when the transistor circuit is turned off.

The base diode 342 decreases the switching time at turn off by removing stored base charge when the input pulse goes negative.

As mentioned above, the tube 102 typically draws 100 amps, varying between 90 and 150 amps. Transistor 330 is driven with a forced current gain of approximately 10. The ferroresonant transformer provides a 6 V 15–20 amp base drive signal. The collectors of each of the transistors of circuits 322, 324, and 326 are combined at point 350 which is coupled to the cathode 106. The transistors are therefore able to meet the tube's current requirements.

It is highly desireable in a pulsed ophthalmic laser system to have maximum control over the laser drive pulses. For example, one advantage of the pulsed transformer drive is that as the input voltage is shut off the output voltage of the transformer goes sharply negative helping to shut off the transistors. However, too deep a reverse voltage could damage the transistor and must be controlled. This is accomplished using the 75 ohm resistors 360 and 362 which are in parallel with the primary windings 302 and 304, respectively. The values of these resistors control the depth of the negative going portion 402 of the switching signal 400 shown in FIG. 4. As mentioned earlier the turn off response of the transistors is also aided by the diode 342 for removal of stored base charge.

The lead 370 running from the transistor switch circuit on the circuit board to the cathode of the tube has a finite length with an inductance associated therewith.

When the high current flowing through the lead is suddenly terminated because the transistors are turned off so sharply, a voltage transient is created by the lead inductance. This transient is capable of damaging the power transistors in the circuits 322, 324 and 326. To remedy this a clamping circuit 380 comprising diode 382 and capacitor 384 is provided across the output of circuits 322, 324 and 326. The energy from the transient is stored in capacitor 384 which then bleeds off the energy slowly during the inter pulse intervals to the main power supply capacitors. By positioning a small compacitor (0.1 microfarad) on the transistor circuit circuit board close to the transistors, little inductance is associated with the clamping circuit itself and the transient is deflected from the transistors.

FIG. 5 is a simplified block diagram of an ophthalmic laser system designated generally 500. Laser light from a laser such as the laser 200 enters the focusing lense assembly 502 onto aiming mirror 504 and then to the target 506. Target 506 in FIG. 5 depicts a conventional light intensity meter which measures the intensity of the laser light incident thereon. This is used during the laser calibration procedure but normally, for ophthalmic lasers, the target is a human eye. Aiming mirror 504 is pivotable and is controlled by the doctor by handle 510.

Focusing of the laser beam to control spot size as it impinges on the target surface within the eye is extremely important. Spot size is controlled manually by the doctor by turning knurled knob 520. Turning of this knob controls the spacing between lenses 522 and 524 within the lense housing 530. When the knob 520 is turned one way or the other the lenses are caused to move toward or away from another in the directions of the double arrow. Such an arrangement of lenses is well known in the prior art. In the present invention spot size is variable from 50 to 1500 microns.

A portion of the laser beam is split off by beam splitter 514 and directed to impinge on photocell 516. Photocell 516 generates a voltage in response thereto which is related to the power of the laser beam and which is used by the computer to determine the power or energy actually delivered to the target during a burst or treatment.

The system 500 further comprises a biomicroscope 540 and objective lens 542 through which the doctor is enabled to see the eye. These are well known in the art. See for example, Britt Corporation's Model 152 Ophthalmic Laser. The doctor controls firing of the laser by a foot switch. Before firing the doctor aims the laser beam which is at low power and adjusts the spot size appropriately for the procedure. The laser system 500 while on is in the aiming mode unless the doctor fires the laser. The doctor is able to see into the eye at the same time that the laser beam is reflected off the mirror 504 into the eye. A conventional shutter arrangement, not shown, is employed to block the line of sight from the doctor's eye to the laser beam during firing of the laser.

Referring now to FIG. 6, an overall block diagram of a control circuit portion 600 of an ophthalmic laser system is shown coupled to a laser such as laser 200. The control circuit comprises a control panel 602, a foot switch 603, a microprocessor controller 604, counter circuit 606 and hardware limiter 608. The microprocessor controller 604 in the preferred embodiment is an Intel 8088 microprocessor chip.

FIG. 7 shows the details of the control panel 602 including the various modes of operation of the laser system. It represents the operator command interface to the laser system. In general the operator commands are entered by depressing an appropriate button on the panel. The control panel is really a custom made keyboard and the commands are digitized and transmitted via bus 610 to the microprocessor controller 604 where they are interpreted and ultimately converted to signals which set or load counters in the counter circuit 606. The counter control signals set the pulse repetition rate, pulse width and exposure time of the control signals sent to the switch 306. The microprocessor controller 604 automatically sets the pulse width of the control signals up to 120 microseconds depending on the mode of operation.

The power switch 702 turns on a slit lamp. The brightness of the slit lamp (not shown, but a conventional device used with the biomicropscope 540 to illuminate the eye so the operator can see) and the panel illumination are controlled by knobs 704 and 706, respectively. The operator can select either the coagulation or perforation modes via buttons 708 and 710, respectively. These modes will be discussed in more detail hereinafter. In the preferred embodiment, the laser system is capable of operating an argon or krypton laser generating three colors: blue/green; green; or red. The color desired is selected by a button in the area 712 of the panel.

The exposure time for any particular treatment can be selected at location 714 and displayed in display areas 716 and 718. When in the coagulation mode the power can be varied at location 720 while in the perforation mode, the pulse repetition rate can be varied at location 722 and displayed at location 724.

When the laser system is on and between treatments the system produces an aiming mode as described earlier. The intensity of the aim beam can be varied at location 726.

Lense assembly 502 further comprises a potentiometer coupled to the knob 520. When the knob is turned the potentiometer changes providing a voltage which is a function of the spot size of the laser beam. The relationship between spot size and voltage is measured and plotted for each model slit lamp and zoom lense combination such as a Zeiss Model 100/16 slit lamp with Britt Corporation zoom lense made for that slit lamp and commercially available. The plotted curve is then described in the software of the microprocessor 604 so that the spot size can be determined from the potentiometer voltage. The spot size is displayed at location 730.

The laser system is capable of being calibrated, a process to be described hereinafter. Calibration is triggered by pressing the button 732. Finally, where a lengthly treatment procedure is required, such as in a pan retinal photocoagulation procedure, a special REPEAT mode is provided which allows treatment bursts at pre-set intervals to reduce operator fatigue. The REPEAT mode is set up at location 740 and will be discussed in more detail hereinafter.

Buttons 744, 746, 748 and 750 cause display area 742 to display various parameters such as cumulative energy (to be described later); aim power; peak power; and tube pressure. Display areas 752 and 754 display the average power delivered and the average power entered for a given burst of laser pulses delivered for a coagulation treatment.

Figure 9:
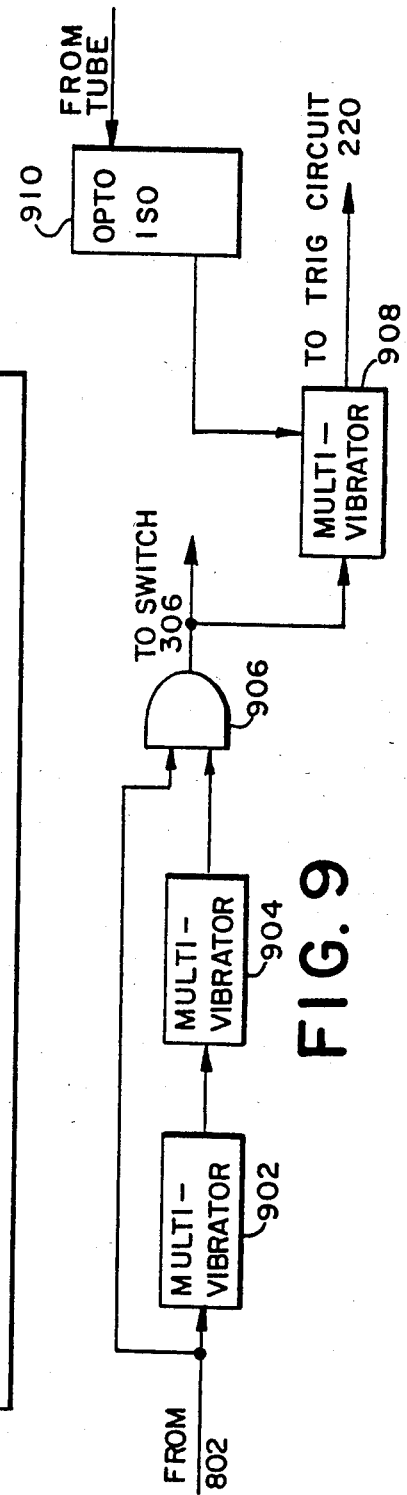
FIG. 9 is a more detailed block diagram of the hardware limiter portion of the control circuit of FIG. 6.

Before discussing the modes of operation of the laser system in more detail reference is made to FIGS. 8 and 9. The control signals are generated by the counter circuit of FIG. 8. In response to the operator commands and mode selection via panel 602, the microprocessor controller 604 automatically determines the proper pulse width and sets counter 802 appropriately. Microprocessor controller 604 also sets counter 804 to produce the proper pulse repetition rate and loads counter 806 with an exposure time count. The exposure time count is displayed at display lcoation 718.

The counters 802 and 804 operate in response to a one MHz clock provided via lead 808. Counter 804 provides periodic output signals at the pulse repetition rate set by the microprocessor. Counter 802 in response to each output signal from counter 804 generates a pulse with the proper pulse width which is transmitted via lead 612 to the hardware limiter circuitry 608.

The output signals from counter 804 are also sent to counter 806 which counts them down from the count loaded therein by the microprocessor. When zero is reached counter 806 automatically stops counter 804.

The functions of all three counter circuits as shown in FIG. 8 are provided by proper connection of an INTEL 8253 integrated circuit.

The hardware limiter circuitry as shown in some detail in FIG. 9 limits the maximum pulse width (no greater than 120 microseconds) and maximum repetition rate (not to exceed 3000 per second). Circuit 608 includes a first one shot multivibrator circuit 902 which is triggered by the output pulses of counter 802. One shot 902 provides a 3 millisecond long output signal to one shot circuit 904. On the rising edge of the output from one shot 902, one shot 904 provides a 120 microsecond long pulse which is combined together with the original input pulse from counter circuit 802 in AND gate 906 to provide the switching signal to switch 306 which in the preferred embodiment is a transistor switch. Since the output of counter 802 is combined with a 120 microsecond pulse to produce the laser pulse the laser pulse cannot exceed 120 microsecond even if through some error the microprocessor 604 sets counter 802 with a longer pulse. Since the 120 microsecond long pulse is only produced at the rising edge of the output of one shot 902 it cannot occur more than 3000 times per second. The circuit of FIG. 9 controls the output of the computer/counter circuit combination to prevent it from producing pulse rates or widths which will damage the laser.

The output from AND gate 906 is also transmitted to one shot multi-vibrator 908 which provides a signal to trigger circuit 120 in FIG. 2 to ionize the laser tube 102. However, if the tube is already in a low power glow mode a resister in the tube power circuit senses the current and a signal is provided to opto isolator circuit 910 which inhibits the one shot 908. Circuit 910 provides isolation between the tube's power supply and the control circuit.

The microprocessor controlled counter circuit design approach is utilized to provide a fail safe feature. When the foot pedal 603 is depressed the microprocessor sets and loads the counters in accordance with the inputs received from the operator through the control panel. One input is the exposure time which is provided as a loaded exposure time count in counter 806. When the count reaches zero the laser stops firing until the foot pedal 603 is depressed again. In the aim mode the beam is continuously on at low power, that is, at a low repetition rate and short pulse width as set by the operator (location 726) and microprocessor 604. No foot pedal is depressed. In this mode (activated whenever the system is on but during pretreatment intervals) the counters 802 and 804 are set appropriately and counter 806 is loaded with a predetermined count number. The microprocessor is programmed to repeatedly reload counter 806 with the predetermined count before the count reaches zero during the aiming mode. If for some reason the microprocessor fails, the aiming beam will go off automatically when the last loaded count reaches zero.

Figure 10:
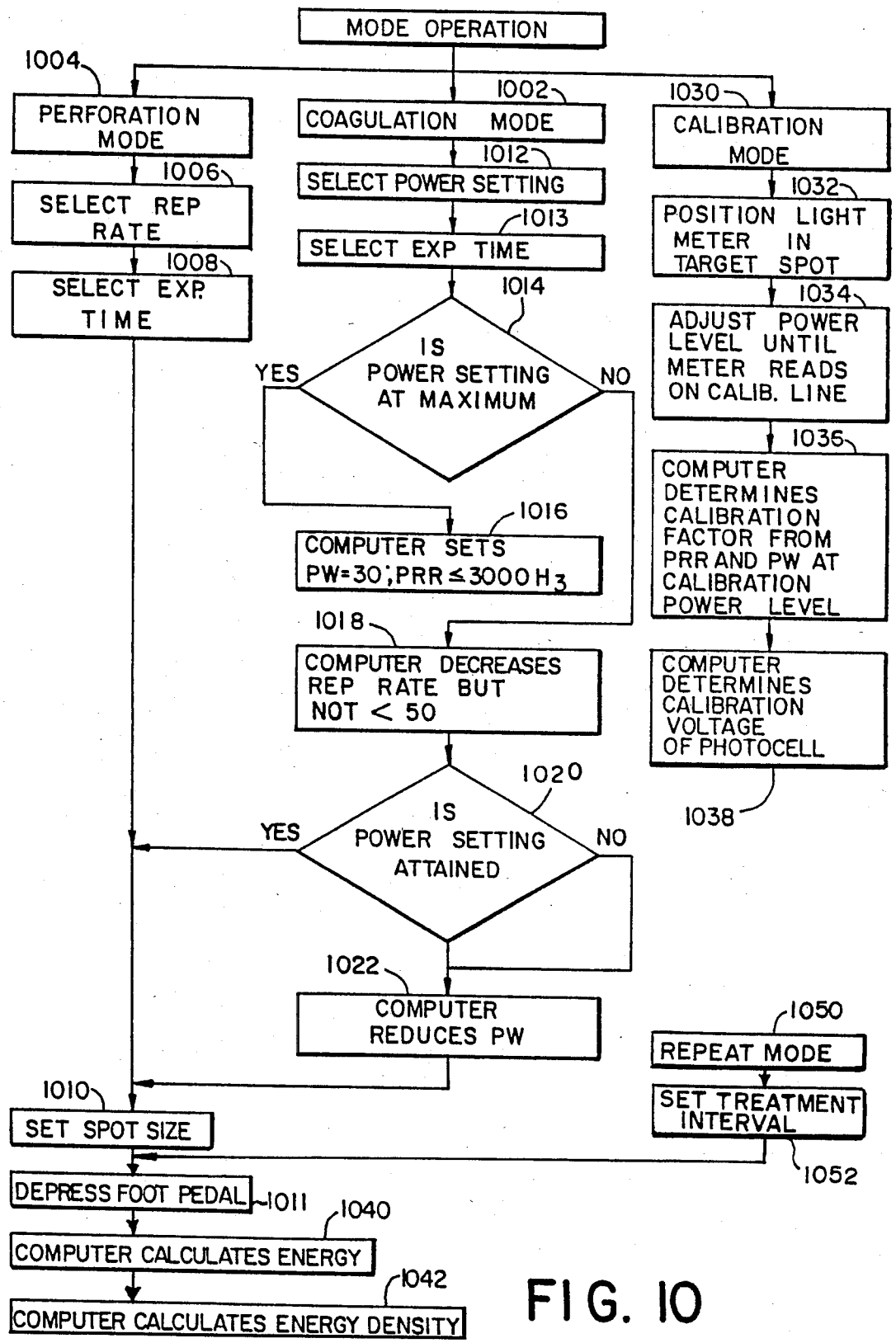
FIG. 10 is a block diagram flow chart showing the operation of the ophthalmic laser system of the present invention for representative modes of operation.

Referring now to FIG. 10, the operator selects either the coagulation mode 1002 or perforation mode 1004. In the perforation mode as explained earlier, it is desirable to provide high power pulses. The operator selects the repetition rate desired 1006 and the exposure time 1008. The microprocessor automatically selects a 120 microsecond pulse width for high power. The operator adjusts the spot size 1010 and when ready depresses the foot pedal 1011. The microprocessor sets counter 802 and 804 and loads counter 806 and then enables the counters. The control pulses are provided to laser 200 which in turn fires the programmed burst of laser pulses to the target.

The coagulation mode operates with smaller pulse widths than the perforation mode. In the coagulation mode the operator selects desired power level 1012 and exposure time 1013. If the selected power setting is at maximum level 1014 the microprocessor selects a pulse width of 30 microseconds and an appropriate pulse repetition rate less than or equal to 3000 Hz to attain the power level 1016. For lower power levels the microprocessor first lowers the repetiton rate. However, the repetiton rate will not be lowered below 50 Hz 1018. If the desired power setting is still not attained 1020 then the microprocessor reduces pulse width 1022. The operator selects the desired spot size 1010 and depresses the foot pedal 1011 and the microprocessor takes over as before.

The laser system of the present invention is equipped with a calibration mode 1030. In this mode, a light intensity meter 506 is positioned in the target location 1032. The operator pushes button 732, then depresses the foot pedal and adjusts the power setting (at location 720) until the light intensity meter indicates that the delivered laser power is at a predetermined power setting for example, 1 Watt 1034. The microprocessor then has the pulse width and repetition rate setting which provides the calibrated power level 1036. For example, $$P_C \alpha \ (PW)_C (PRR)_C$$

For a particular burst of laser output pulses to be used for treatment the power is $$P_T/P_C \alpha \ (PW)_T (PRR)_T / (PW)_C (PRR)_C.$$

Where $P_C = 1$ Watt, $P_T$ in watts is the above ratio of (pulse width)(pulse repetition rate) products. The equation can be rewritten as $P_T = (K)(PW)_T(PRR)_T$ where K is a constant incorporating $1/(PW)_C(PRR)_C$. The laser system uses this equation to set up the pulse width and repetition rate of a burst of laser pulses to meet the power input selected by the operation in the coagulation mode at location 720. Also, using this equation, the laser system, for either the coagulation mode or performation mode, calculates the average power entered for each burst and display it at location 754.

The output of the photocell 516 is calibrated at the same time as $PW_C$ and $PRR_C$ 1038. The calibrated photocell output voltage $V_C$ is related to $P_C$. Part of the proportionality is due to the percentage of power split off by beam splitter 514. The average power actually delivered during any given treatment (either coagulation or perforation) as determined by the photocell voltage can be determined from the voltage output of the photocell during the treatment, $V_T$, $V_C$ and $P_C$. The average power delivered during a treatment burst as determined from $V_T$, $V_C$ and $P_C$ is displayed at location 752.

The energy delivered is related to power by multiplying the average power delivered by the amount of time over which the power is delivered. The energy delivered for any given burst is determined by multiplying the power delivered as determined by the photocell voltage and the exposure time set by the operation at location 714, displayed at 716. Cumulative energy for a total treatment involving a plurality of bursts is determined by adding up the energy delivered for each burst.

The energy density for each burst is determined by dividing the energy delivered as determined above by the spot size as determined by the potentiometer voltage 1042. If the diameter of the spot is reduced by a factor of two the area is reduced by a factor of 4 and the energy density increases by a factor of 4. Realizing the effects of reducing spot size when performing perforations or coagulation procedures is very important for proper treatment and avoidance of unnecessary eye damage.

As mentioned earlier, in some treatment procedures such as in a pan retinal procedure, many bursts of laser power are required to complete the procedure. Where, as in the prior art, it is necessary for the operation to lift a foot from the foot pedal and then reapply the foot to depress the foot pedal for each firing the laser it can become very tiring for the operator. This, of course, is highly undesireable.

Referring to FIGS. 7 and 10, the present invention overcomes this problem by providing a REPEAT mode of operation. After the operator has selected either the perforation mode 1004 or coagulation mode 1002 and made the necessary selections (e.g. steps 1006 and 1008 or 1012 and 1013), the operator depresses the repeat mode button 770 in location 740. Then using the set button 772, the operator selects a time interval which is displayed in area 774. When the desired interval is displayed, the operator depresses the enter button 776. Now the repeat mode is set up. See steps 1050 and 1052 in FIG. 10.

Following the set up of the REPEAT mode, the operator depresses the foot pedal 603 moving it from the off position to the on position 1011. As long as the foot pedal 603 remains depressed, the burst of laser pulses set up in the perforation mode 1004 or coagulation mode 1002 before the button 770 was depressed will automatically be repeated at the interval selected by buttons 772 and 776. The bursts will continue as long as the foot pedal 603 is depressed by the operator. Of course other poer control means besides a foot pedal could be used, e.g., a manually depressed button.

When the treatment is finished the button 760 can be pressed and a history of the treatment is printed out on a printer not shown.

What is claimed is:

1. A pulsed laser system comprising:
   a laser tube having electrodes;
   a power switching means coupled to the electrodes of said laser tube for energizing said laser tube in response to a series of periodic control signals to generate a burst of laser output signals;
   power control means movable between an off position and on position for activating said laser tube by enabling said generating means to apply said control signals to said power switching means in said on position; and repeat means coupled to said generating means for automatically repeating at a predetermined interval said burst of laser pulses generated within a preselected exposure time while said power control means is held in said on position.

2. The pulses laser system of claim 1 wherein said power control means comprises a foot pedal.

3. The pulsed laser system of claim 1 wherein said laser system is radiation cooled.

* * * * *

UNITED STATES PATENT AND TRADEMARK OFFICE
CERTIFICATE OF CORRECTION

PATENT NO.  : 4,601,037

DATED       : July 15, 1986

INVENTOR(S) : John J. McDonald

It is certified that error appears in the above-identified patent and that said Letters Patent is hereby corrected as shown below:

Column 10, after line 27 and before line 28 which starts with the words "power control means" for the claim reference numeral "1", insert the following:

-- means for generating said control signals and for controlling the repetition rate, pulse width and exposure time thereof; --.

Signed and Sealed this

Fourteenth Day of April, 1987

Attest:

DONALD J. QUIGG

*Attesting Officer*  *Commissioner of Patents and Trademarks*